United States Patent [19]

Bennett

[11] Patent Number: Plant 6,789

[45] Date of Patent: May 9, 1989

[54] MINIATURE ROSE PLANT, NAMED 'BRIAN LEE'

[75] Inventor: Cecilia L. D. Bennett, Chula Vista, Calif.

[73] Assignee: Susan Mae O'Brien, Chula Vista, Calif.

[21] Appl. No.: 151,254

[22] Filed: Feb. 1, 1988

[51] Int. Cl.[4] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant named 'Brian Lee', which is characterized by its red-mauve blend blooms, ranging from near Garnet Lake to near Dianthus Purple. The blooms are usually borne one to a stem with hybrid tea form. The bush is vigorous, well-branched and produces moderate to heavy quantity of blooms.

1 Drawing Sheet

The present invention relates to a new and distinct variety of a hardy dwarf, bush plant of the miniature class; the variety being primarily characterized as a mauve blend.

The variety is further characterized by:

Long stemmed blooms of hybrid tea-type form, borne usually one to a stem but on occasion in sprays of 3 to 5 or more. The blooms are held very erect and well above the foliage.

It has a moderate amount of 'fruity' fragrance.

The plant ranges in height from 24 to 36 inches (approximately 60 to 90 cm). The canes are sturdy and erect with moderate branching and medium to heavy foliage covering. The plant is an average to above average bloomer that does well either in the greenhouse or outdoors.

The plant has good growth habits, well-shaped and attractive, bearing numerous leaflets of average size. I have found this new variety to be easily asexually reproduced by cuttings.

The seed parent was Carrousel (U.S. Plant Pat. No. 1,066), and the pollen parent was Plum Duffy (miniature, mauve; Cecilia Bennett; introduced by Tiny Petals Nursery, 1978). It differs from its seed parent in the following ways. It is a miniature rose in the mauve blend class; and Carrousel is a grandiflora in the medium red class. It differs from its pollen parent in the following ways. It has a plant size of greater than 24 inches high when fully mature, and the bloom color ranges in shades of near Garnet Lake to near Dianthus Purple; whereas Plum Duffy has a plant size of 12 to 15 inches fully mature, and the bloom color ranges in shades of near Campanula Violet to near Heliotrope.

The descriptive matter which follows pertains to roses grown and color values observed in plants and newly opened blooms in the months of March through August 1987. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Brian Lee', the following is a detailed description thereof in outline; all major color plate identifications being by reference to the British Colour Council Horticultural Colour Chart, except where common terms of color definition are employed.

Type: Hardy, spreading, greenhouse or outdoor, decorative or exhibition potted plant.

Class: Miniature.

Variety name: Brian Lee.

Flowers borne: Usually one to a stem but on occasion in sprays of 3 to 5 or more on erect stems with foliage well below the blooms.

Quantity of bloom: Moderate to heavy outdoors or greenhouse grown.

Bud:

*Peduncle.*—Variable in length (20 to 35 mm); average diameter and sturdy; ranging in color from near Scheeles Green (860/3 to 860/2 page 860) to near Lettuce Green (861/3 to 861/2 page 861) with an occasional tinting of bronze.

*Hairs.*—Extremely small and numerous with reddish color; located over the entire surface of the peduncle and sepals, but not present on the calyx tube.

*Calyx.*—Same color as the peduncle; without hairs.

*Opening.*—Opens well in all weather.

Bloom:

*Size when fully opened.*—Average to large for a miniature variety (40 to 50 mm).

*Petalage.*—Double; averaging 25 to 30 petals, arranged regularly, plus petaloids (5 to 10 or more).

*Form.*—Urn-shaped to ovoid as the bloom progresses. The petals remain at first somewhat cupped with the apex and/or margins reflexed outward, becoming at maturity more loosely cupped; and the petals reflex more tightly (quilling), until each row of petals forms five pointed star.

Petals:

Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate with some occasional irregularities.

Color: Newly opened flowers from plants grown outdoors (March through August 1987), Chula Vista, Calif.

*All petals.*—Upper Surface — Ranging from near Garnet Lake (828/3 to 828/1 page 172) to near Dianthus Purple (730/2 to 730 page 160) with a tip of near Mimosa Yellow (602/1 to 602 page 602). Under Surfaces — Same as Upper Surfaces.

*General color effect.*—Newly opened flowers — Overall reddish mauve to deep mauve. Color darkens with aging of the blooms to dark mauve after 5 to 7 days. Cut blooms at living room temperature 4 to 7 days or longer.

Reproductive organs:

*Stamens.*—A generous amount arranged uniformly around the pistil.

*Filaments.*—Varying in length with shorter filaments more proximal to the pistil; golden yellow including the anthers.

*Pollen.*—Abundant.

*Pistil.*—Long, abundant and spreading; pale yellow at the base to reddish at the top with pale yellow caps on the styles.

*Ovaries.*—All encased in the calyx.

*Hips.*—Some.

*Seeds.*—3 to 5 or more in each hip.

*Sepals.*—Permanent; spear-shaped; open as the bloom opens, recurving against the peduncle, when the bloom is fully opened.

Foliage:

*Leaves.*—Five to seven leaflets on the average; medium size for a miniature rose plant.

*Leaflets.*—Broad ovate-shaped.

*Margin.*—Very serrated with tinting of bronze, especially noticeable on the newer foliage.

*Color.*—Ranging from near Spinach Green (0960/1 to 0960/3 page 187) to near Scheeles Green (860 to 860/2 page 175) with occasional bronzing of the margins which is reddish on the newer stems and foliage. The upper surfaces have a semi-glossy finish, and the under surfaces have a matte finish of a slightly lighter shade than the upper surfaces.

*Rachis.*—Medium strength; upper surface is grooved with very small reddish hairs over the length of it. Under surface has few if any hairs but does contain 3 to 5 small thorns on average.

*Stipules.*—Varying in length from small to medium; average width; tapering auricles angled outward at about 45 degrees.

Growth:

*Habit.*—Dwarf, bushy; average to tall height for a miniature rose plant (24 to 36 inch).

*Growth.*—Upright and well-branched.

*Canes.*—Ranging from near Spinach Green (0960/1 to 0960/3 page 187) to near Scheeles Green (860 to 860/2 page 175) with some occasional bronzing; medium diameter; sturdy; held erect.

*Main stems.*—Same as canes.

*Thorns.*—Averaging 5 to 10 per 10 cm on the main stems and fewer on the branches. Reddish in color; small to average in size; hooked slightly downward.

*Branches.*—Color — Same as canes.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant, named 'Brian Lee' of hardy, dwarf, bushy, well-branched and attractive in appearance with vigorous growth, substantially as illustrated and described; it is further characterised by its blooms of reddish-mauve, ranging from near Garnet Lake to near Dianthus Purple, with hybrid tea-type form that are usually borne on to a stem but on occasion may come in sprays of 3 to 5 or more.

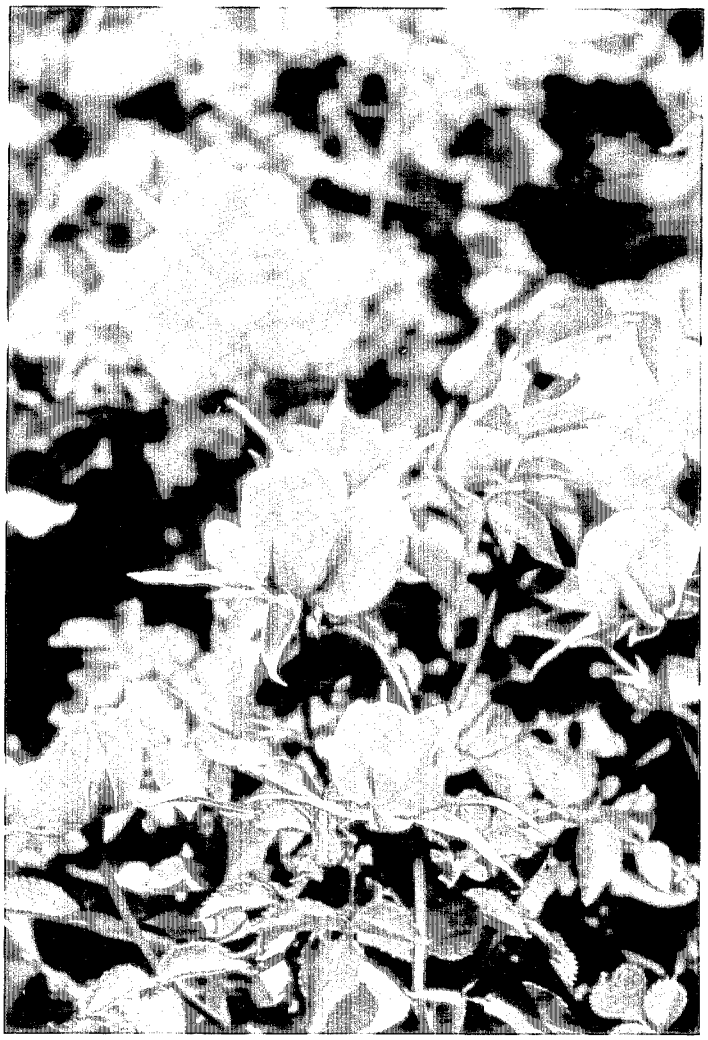

* * * * *